United States Patent [19]

Jacobson

[11] Patent Number: 4,560,806
[45] Date of Patent: Dec. 24, 1985

[54] PROCESS AND CATALYST USEFUL IN THE PRODUCTION OF GLYCOL ALDEHYDE

[75] Inventor: Stephen E. Jacobson, Morristown, N.J.

[73] Assignee: The Halcon SD Group, Inc., New York, N.Y.

[21] Appl. No.: 596,994

[22] Filed: Apr. 5, 1984

Related U.S. Application Data

[63] Continuation-in-part of Ser. No. 508,704, Jun. 28, 1983, abandoned.

[51] Int. Cl.[4] .................. C07C 45/49; C07C 47/19
[52] U.S. Cl. .................................................. 568/462
[58] Field of Search ..................... 568/462, 883, 882

[56] References Cited

U.S. PATENT DOCUMENTS

| | | | |
|---|---|---|---|
| 3,920,753 | 11/1975 | Yukawa et al. | 568/458 |
| 4,291,179 | 9/1981 | Goetz et al. | 568/458 |
| 4,382,148 | 5/1981 | Drent | 568/458 |
| 4,405,814 | 9/1983 | Carroll et al. | 568/462 |
| 4,477,685 | 10/1984 | Chan | 568/462 |

*Primary Examiner*—Werren B. Lone
*Attorney, Agent, or Firm*—William C. Long; Riggs T. Stewart; Daniel R. Zirker

[57] ABSTRACT

An improved transition metal-phosphine-amide hydroformylation catalyst is disclosed having a substantially increased solubility in non-polar organic solvents, thereby preventing migration of the catalyst into the glycol aldehyde product during the hydroformylation process and subsequent separation operations, greatly facilitating and improving the catalyst separation and recycle operations.

13 Claims, No Drawings

PROCESS AND CATALYST USEFUL IN THE PRODUCTION OF GLYCOL ALDEHYDE

This application is a continuation-in-part of Ser. No. 508,704 filed June 28, 1983, now abandoned.

BACKGROUND OF THE INVENTION

This invention is related to a process and accompanying catalyst for the preparation of glycol aldehyde, and more particularly is related to the preparation of glycol aldehyde from the reaction of formaldehyde, carbon monoxide and hydrogen in the presence of a class of rhodium phosphine-amide catalysts in a wide variety of organic solvents. The glycol aldehyde product is later hydrogenated to ethylene glycol.

DESCRIPTION OF THE PRIOR ART

Glycol aldehyde is a valuable intermediate in many organic reactions, and is particularly useful as an intermediate in the production of ethylene glycol through a catalytic hydrogenation process.

The reaction of formaldehyde with carbon monoxide and hydrogen in the presence of a variety of catalysts at elevated temperatures and superatmospheric pressures is a well known reaction and yields glycol aldehyde, together with methanol, as well as lesser amounts of polyhydroxy compounds which can be subsequently separated by proper separation procedures. For example, U.S. Pat. No. 2,451,333 describes the reaction of formaldehyde, carbon monoxide and hydrogen over a cobalt catalyst to produce ethylene glycol. U.S. Pat. No. 3,920,753 discloses the production of glycol aldehyde by the reaction of formaldehyde, carbon monoxide and hydrogen in the presence of a cobalt catalyst under controlled reaction conditions; however, the process produces relatively low yields of product. Japanese Pat. No. J57-118,527 describes the production of glycol aldehyde using a ruthenium catalyst system. European Patent Application No. 002,908 describes a process for the production of glycol aldehyde from the reaction of formaldehyde, in the presence of a rhodium-triphenyl phosphine ligand catalyst, with carbon monoxide and hydrogen, in a tertiary amide solvent. This reference further suggests that glycol aldehyde is preferably extracted from a water immiscible hydroformylation solvent. However, the proposed method suffers from the drawback of limiting the choice of hydroformylation solvent to the class of water immiscible solvents, whereas the most effective hydroformylation solvents, such as acetonitrile, are very water soluble. Furthermore, when extracting glycol aldehyde with an aqueous extractant, even when using a water-immiscible solvent, a substantial amount of the expensive rhodium catalyst migrates into the water phase and is lost, thereby decreasing both the amount and the activity of the remaining catalyst.

U.S. Pat. No. 4,291,179 describes a similar reaction for the production of acetaldehyde in which trifluoroacetic acid is added to produce glycol aldehyde. U.S. Pat. No. 4,356,332 describes the preparation of ethylene glycol from the reaction of synthesis gas and formaldehyde, using a rhodium or cobalt catalyst in the presence of a substantially inert, oxygenated hydrocarbon solvent. European Patent Application No. 82/200,272.1 describes a process for the preparation of glycol aldehyde which comprises reacting formaldehyde, hydrogen and carbon monoxide in the presence of either a rhodium or cobalt containing catalyst precursor, together with a strong protonic acid, a tertiary amide solvent and a triaryl phosphine. U.S. Pat. No. 4,200,765 describes a process of preparing glycol aldehyde involving reacting formaldehyde, carbon monoxide, and hydrogen in a tertiary amide solvent in the presence of a catalytic amount of rhodium in complex combination with carbon monoxide, using triphenylphosphine as the preferred catalyst promoter. U.S. Pat. No. 4,405,814 discloses a similar process for the production of glycol aldehyde, incorporating a tertiary organophosphorous or arsenic moiety into the rhodium catalyst together with a basic organo amine. U.S. Pat. No. 4,405,821 discloses still another similar process involving carrying out the reaction in the presence of a glycol aldehyde yield enhancing phosphine oxide.

All of the known prior art processes for the production of glycol aldehyde have characteristically produced a mixture of reaction products, such as glycerine, glyceraldehyde and methyl alcohol. Unfortunately, these processes are encumbered by the need for expensive and time-consuming separation procedures, and also suffer from a consequent reduction in the amount of eventual end product produced, facts that the patent literature has tended to gloss over. Such problems are particularly evident in the production of glycol aldehyde from the hydroformylation of formaldehyde, where the problems of aldol condensation reactions and of acetal formation hamper the subsequent separation of the product from the catalyst, and the formation of catalyst poisoning amines occurs, particularly when the preferred amide solvents are used. Amines also serve to catalyze the aldol condensation of glycolaldehyde with formaldehyde and other aldehydes.

An additional flaw of the prior art processes incorporating transition metal-phosphine catalysts has been the inability to recover a satisfactory amount of the expensive metal, e.g., rhodium, catalyst after the hydroformylation reaction, thus frustrating the subsequent recycle and reuse of the catalyst. In the propylene hydroformylation of n-butyraldehyde large excesses of triaryl phosphine (U.S. Pat. No. 4,277,627) coupled with the introduction of small quantities of diarylalkylphosphine (U.S. Pat. No. 4,260,828) were used to stabilize the resulting rhodium compound. However, in the instant formaldehyde hydroformylation process such an excess of either alkyl or aryl phosphine is not feasible, due to the resulting substantial increase in methanol selectivity at the expense of glycol aldehyde selectivity when operating with an increased phosphine concentration, i.e., above a 3 to 1 phosphine to rhodium ratio.

Another serious problem to be overcome is that the particularly preferred rhodium-phosphine-amide catalysts disclosed in parent copending U.S. application Ser. No. 508,704, as well as earlier prior art catalytic systems which are active in the formaldehyde hydroformylation to glycol aldehyde, are ineffective in catalyzing the subsequent hydrogenation of glycol aldehyde to ethylene glycol. Furthermore, it has been found that the preferred rhodium-phosphine-amides disclosed in Ser. No. 508,704 also have a tendency to migrate into the glycol aldehyde product phase during extraction, and it is essential, both from the standpoint of saving the expensive rhodium catalyst and also from prolonging the activity of the catalyst, to prevent this migration from occurring. In copending U.S. patent application Ser. No. 597,003, filed concurrently herewith, now U.S. Pat. No. 4,496,781, issued Jan. 29, 1985, the disclosure of which is incorporated by reference, an improved process has been developed using the particularly preferred lipophilic catalysts disclosed herein to extract the glycol aldehyde into an aqueous phase from which it can be purified and then hydrogenated to the desired ethylene glycol.

Thus, it is an object of this invention to provide an improved process for the hydroformylation of formaldehyde to glycol aldehyde and its subsequent hydrogenation to ethylene glycol which has high conversions and selectivities, using a variety of non-amide solvents from the reaction of formaldehyde, carbon monoxide and hydrogen feedstocks.

It is another object of this invention to provide a process wherein the glycol aldehyde and the transition metal-phosphine-amide catalyst can be easily separated and extracted or recycled from the reaction product mixture in an effective industrial operation.

It is still another object of this invention to develop a hydroformylation catalyst which is substantially incapable of migrating into the glycol aldehyde product phase during product separation, thus preventing the loss of the expensive catalyst.

It is still another object of this invention to provide a catalyst for the hydroformylation of formaldehyde which is capable of being recycled a substantial number of times without experiencing a significant loss in catalytic activity.

SUMMARY OF THE INVENTION

Accordingly, the invention provides for an improved process and accompanying catalyst for the production of glycol aldehyde comprising contacting formaldehyde, carbon monoxide and hydrogen with an effective polar organic solvent, or, a mixture of polar-non-polar organic solvents in a reaction zone, under suitable superatmospheric pressure and elevated temperature conditions, in the presence of a rhodium, cobalt, or ruthenium-containing catalyst, most preferably rhodium, including mixtures thereof; the catalyst further including a carbon monoxide ligand and a phosphine ligand incorporating therein an ancillary tertiary amide group. The presence of the phosphine-amide ligand in the resultant metal carbonyl complex permits the formation of complexes having the formula $MX_x(CO)_y[P(R_1)_2R_2-C(O)-NR_3R_4]_z$, wherein M is an element selected from the group of rhodium, cobalt, and ruthenium; X is an anion, preferably a halide, a pseudohalide, a hydride or a deprotonated strong carboxylic acid; P is phosphorous; $R_1$ is an aromatic or aliphatic group of 1–20 carbon atoms, preferably aromatic; $R_2$ is an organo group containing from 0 to 20 carbon atoms of either aliphatic or aromatic nature which may include oxygen, nitrogen or sulfur atoms, which atoms may be directly bonded to the amide C(O)N carbon, or nitrogen; $R_3$ and $R_4$ are aliphatic or aromatic groups containing from 1 to 100 carbon atoms; the resultant compound being characterized by the absence of hydrogen on the amide nitrogen atom and the additional limitation that if $R_2$ is bonded to the amide nitrogen, then either $R_3$ or $R_4$ is bonded to the amide carbon; x ranges from 0 to 3, y ranges from 1 to 5, and z from 1 to 4. Surprisingly, it has been found that the usage of a preferred class of lipophilic phosphine-amides having structures as indicated above, wherein at least one of $R_3$ and $R_4$ range from about 10 to about 100 carbons, and, most preferably, the compound $PPh_2CH_2CH_2C(O)N(CH_3)[(CH_2)_{17}CH_3]$ (Ph is phenyl) and the like are particularly active catalysts for the hydroformylation reaction, while also displaying a substantial solubility in non-polar organic solvents, thereby greatly improving subsequent product and catalyst separation and recycling operations. The usage of this particular class of complexes permits a wide variety of desirable organic polar compounds such as nitriles, ketones, ethers and the like, as well as mixtures, to be effective solvents in the process, and further permits the most preferred process scheme set forth in Ser. No. 597,003, now U.S. Pat. No. 4,496,781, thereby producing high conversions and selectivities to glycol aldehyde and further assisting in an effective product recovery and a catalyst purification and recycling cycle.

DETAILED DESCRIPTION OF THE INVENTION

The process of the present invention can be accomplished by contacting formaldehyde, carbon monoxide, and hydrogen with an effective polar organic solvent, or, a mixture of polar-non-polar organic solvents, in the presence of a transition metal, e.g., rhodium, ruthenium or cobalt-containing catalyst including various mixtures thereof, the catalyst complex further including a carbon monoxide ligand and also having as a substituent a phosphine ligand incorporating an ancillary tertiary amide group, in the presence of elevated temperatures and superatmospheric pressures, that is, under general conditions suitable for hydroformylation with the particular catalyst chosen. Most preferably, the hydroformylation process follows the scheme set forth in copending U.S. patent application Ser. No. 597,003, now U.S. Pat. No. 4,496,781, describing a method of hydroformylation which can also effectively recover and recycle a still active catalyst without the drawbacks of the prior art processes. A high boiling non-polar organic solvent which is immiscible with glycol aldehyde, such as toluene or xylene, is added to the reaction zone together with an effective low boiling polar organic solvent, such as acetonitrile, the latter being a particularly effective hydroformylation solvent. The resulting effluent is then separated to remove the low boiling polar solvent, while the remaining non-polar higher boiling solvent, together with the glycol aldehyde product, separates into two phases. Due to the difference in solubility of the solvent and glycol aldehyde, the glycol aldehyde is precipitated out of solution while the rhodium catalyst remains in the solvent or xylene phase. The two phases are then separated, with the xylene phase containing the catalyst recycled back to the hydroformylation reactor and the glycol aldehyde product, which is substantially free from the rhodium catalyst, is separated and later hydrogenated. Such a process, however, requires a catalyst which is both effective for the hydroformylation reaction, while also being easily separable and capable of retaining its catalytic activity after processing. This requirement is a particularly troublesome point, since during product separation the preferred rhodium-phosphine-amides tend to migrate into the glycol aldehyde layer, thereby causing a substantial loss of expensive catalyst, as well as a substantial decrease in catalytic activity on recycling. Although in the prior art literature the difficulties of the product separating operation are either ignored or allegedly solved by the particular solvent system disclosed, it is believed that there are to date no commercial embodiments of these processes, and that the inability of the art to develop an effective separation process is the major reason. Thus, there is a great need not only for an effective hydroformylation process and accompanying active recyclable catalyst, but also for an effective separation process.

A major problem with this reaction as practiced by the prior art has been that glycol aldehyde tends to form acetals, a reaction typical of aldehydes. Since there is a primary alcohol group present in the molecule, this compound can easily form semi-acetals and acetals with itself in the form of, for example, linear and cyclic-acetals such as are represented by the following structures.

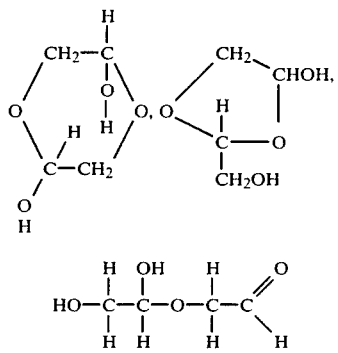

In addition, glycol aldehyde also forms acetals and semi-acetals with methanol, and if present, ethylene glycol. Acetals are resistant to hydrogenation, as well as possessing high boiling points, and therefore can present a difficult process impediment to ethylene glycol formation. Also, the glycol aldehyde product can react with either formaldehyde or with itself through the mechanism of aldol condensation. The reactions can also be inhibited by the product glycol aldehyde which can form bidentate ligands with the coordination metal, i.e., rhodium, and thereby displace a monodentate phosphine ligand.

Surprisingly, it has been discovered that these and other related problems can be substantially eliminated through the use of a novel coordination metal compound, e.g., by the use of a coordination metal, most preferably rhodium, phosphine ligand having incorporated therein an ancillary tertiary amide group, which forms a catalyst which can hydroformylate formaldehyde to glycol aldehyde in very high selectivities, and, surprisingly, in the absence of an amide solvent and which is also operative in a variety of polar organic solvents, as well as non-polar solvents, and various mixtures thereof.

A particularly broad class of metal complexes or precursors which have been found to be suitable as catalysts for the hydroformylation reaction and the subsequent separation and recycle can be represented by the equation:

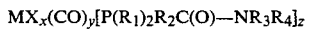

wherein M is an element selected from the group of rhodium, cobalt and ruthenium, including mixtures thereof, X is an anion which can be a halide, a pseudohalide, a hydride or a deprotonated strong carboxylic acid, P is phosphorous, $R_1$ is an aliphatic, aromatic, or a mixture thereof group of 1–20 carbon atoms attached directly to the phosphorous atom, $R_2$ is an organo group containing from 0 to 20 carbon atoms of either aliphatic or aromatic nature, and may include such atoms as oxygen, nitrogen, sulfur and the like, which atoms may also be directly attached to the amide carbon or nitrogen; $R_3$ and $R_4$ are organic, aliphatic or aromatic moieties of 1 to 100 carbon atoms, and most preferably, at least one of $R_3$ and $R_4$ will represent an aliphatic moiety possessing about 10 to about 100 carbon atoms; the resultant amide moiety being characterized by the absence of hydrogen on the amide nitrogen and the additional limitation that if $R_2$ is bonded to the amide nitrogen, then either $R_3$ or $R_4$ is bonded to the amide carbon; x ranges from 0 to 3, y ranges from 1 to 5, and z from 1 to 4. Most preferably, the incorporation of a lipophilic phosphine-amide having the structure $PPh_2CH_2CH_2C(O)N(CH_3)[(CH_2)_{17}CH_3]$ or similar thereto, in conjunction with a rhodium complex are both active catalysts for the hydroformylation reaction and also are particularly soluble in non-polar organic solvents, thereby greatly facilitating the subsequent product separation operations. The synthesis of such a preferred class of catalysts has involved attaching an "organic tail" into the ligand, thus making the ligand lipophilic, that is, a molecule which has a substantial solubility in a non-polar medium even though possessing a substantially polar moiety within its structure. Such a concept is believed novel to carbonylation chemistry, and is accomplished by having either of or both $R_3$ and $R_4$ comprise a long aliphatic chain, preferably, from at least about 10 to about 100 carbons in length. Surprisingly, the addition of such a tail to the phosphine-amide has made possible an effective catalyst separation process in which substantially all of the expensive catalyst is prevented from migrating into the glycol aldehyde phase; in fact, less than 100 ppm of rhodium tend to migrate to the glycol aldehyde phase in the preferred process of the invention, as contrasted with about 1000 to 1500 ppm, using the preferred phosphine-amides disclosed in Ser. No. 508,704.

The anion element X in the aforementioned complex can be a hydride, a halide such as chloride, bromide, iodide or fluoride, as well as pseudohalides which exhibit halide like properties in forming coordinate compounds and the like, including substituents such as $NCS^-$, $NCO^-$, $CN^-$, $NCSe^-$, $N_3^-$,

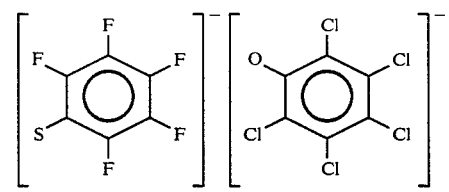

and the like, or a deprotonated strong carboxyclic or sulfonic acid substituents such as trifluoroacetate, trifluoromethanesulfonate, methanesulfonate, toluenesulfonate and the like. The preferred anion containing moieties are chloride, trifluoroacetate and hydride. Alternatively, an anionic rhodium species can be generated in which no anionic element X is present.

The $R_1$ group, in the broadest embodiment, represents either an alkyl, an aryl group or a mixture thereof, the alkyl group containing from 1–20 carbon atoms, with the suitable aryl moieties being phenyl and substituted phenyls, other polyaromatics and substituted polyaromatics and the like. When cobalt is the coordinating metal ligand of choice, it is preferred to use alkyl substituted phosphine, whereas when rhodium or ruthenium is the chosen metal it is preferred to have $R_1$ be phenyl or another aryl moiety.

The $R_2$ group, in the broadest embodiment, represents an organo group containing from 0 to 20 carbon atoms, preferably from 1 to 2 carbon atoms, and is preferably free from acetylenic unsaturation. $R_2$ can be saturated aliphatic, alkenyl, or aromatic and can be either a hydrocarbyl group containing only carbon and hydrogen, or, a substituted hydrocarbyl group containing in addition to atoms of carbon and hydrogen additional atoms such as nitrogen, oxygen, sulfur and the halogens, which additional atoms can also be present in various groups such as alkoxy, aryloxy, carboalkoxy, alkanoyloxy, halo, trihalomethyl, cyano, sulfonylalkyl and the like groups which contain no active hydrogen atoms. Most preferably, $R_2$ is comprised of aliphatic groups containing only carbon and hydrogen.

Illustrative of suitable $R_1$ and $R_2$ moieties are hydrocarbon alkyls such as methyl, ethyl, propyl, isobutyl, cyclohexyl, and cyclopentyl; hydrocarbon alkenyl moieties such as butenyl, hexenyl, cyclohexenyl; alkyl or alkenyl moieties having aromatic substituents such as benzyl, phenylcyclohexyl and phenylbutenyl; and substituted-hydrocarbyl moieties such as 4-bromohexyl, 4-carbethoxybutyl, 3-cyanopropyl, chlorocyclohexyl and acetoxybutenyl. Aromatic moieties are exemplified by hydrocarbyl aromatic groups such as phenyl, tolyl, xylyl, p-ethylphenyl, and substituted hydrocarbyl aromatic groups such as p-methoxyphenyl, m-chlorophenyl, m-trifluoromethylphenyl, p-propoxyphenyl, p-cyanophenyl, o-acetoxyphenyl and m-methyl-sulfonylphenyl.

$R_3$ and $R_4$ represent organo groups of 1 to 100 carbon atoms, preferably at least one being from 10 to 100 carbons, and can be either aromatic, or preferably aliphatic in nature. Suitable groups are the saturated aliphatics of both a cyclic or a linear makeup, aromatics, preferably mononuclear aromatics, and the like. It is most preferred that $R_3$ and $R_4$ be comprised of only carbon and hydrogen atoms. It is also most preferred that the amide moiety in the resultant phosphine ligand be characterized by the absence of hydrogen on the amide nitrogen atom; e.g. tertiary amide groups are most preferred. In the case where $R_2$ is bonded to the nitrogen, instead of the amide carbon, then either $R_3$ or $R_4$ is bonded to the amide carbon. A second organophosphine group can also be incorporated into one or both of the $R_3$ or $R_4$ groups.

The transition metal compound suitable for use in the reaction is selected from rhodium, cobalt or ruthenium, as well as various mixtures thereof, and most preferably is a rhodium compound, complex, or salt. The metal compound may be deposited or affixed to a solid support such as a molecular sieve, zeolite, activated carbon, alumina, silica, an ion exchange resin, an organic polymeric resin, or as an insoluble rhodium oxide, but most preferably is used as a homogeneous complex in solution.

A representative phosphine-amide ligand can be synthesized through a modification of the method disclosed by Meek et al, J. Chem. Soc. (Dalton), 1011, 1975, in which a phosphorous hydrogen bond cleanly adds to the carbon-carbon double bonds of vinyl derivatives in the presence of free radicals such as 2,2'-azobis (2-methylpropionitrile) (AIBN), e.g.:

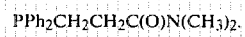

In this case the resulting phosphine exists as a white solid at room temperature. Alternatively, a vinyl amide can be reacted with the secondary phosphine as above. The phosphine-amide can also be synthesized by other routes, such as by photochemistry or by amination of a phosphine ester.

The synthesis of the preferred class of phosphine-amide ligands, particularly the most preferred species $PPh_2CH_2CH_2C(O)N(CH_3)[(CH_2)_{17}CH_3]$, is preferably accomplished by the amidolysis of $PPh_2CH_2CH_2C(O)OC_2H_5$ by $N(H)(CH_3)[(CH_2)_{17}CH_3]$ using sodium methoxide as a catalyst. A temperature of about 50° C. to 150° C. for about 1 to 50 hours and a 1 to 1 to a 2 to 1 phosphine to amine ratio have been found to be satisfactory.

The major product of the hydroformylation reaction is glycol aldehyde, with the major byproduct being methanol. The precise manner of contacting the reactants is not critical, as any of the various procedures known in the art for this type of reaction can be used so long as there is suitable efficient gas-liquid contact. Thus, for example, the process may be carried out by contacting a solution of formaldehyde together with the particular catalyst and solvent and a mixture of carbon monoxide and hydrogen at the selected conditions. Alternatively, the solution of formaldehyde may be passed over and through the catalyst in a trickle phase under a mixture of carbon monoxide and hydrogen at the selected conditions of temperature and pressure. It will, of course, be recognized that the illustrated reactants are capable of undergoing other reactions besides the primary one, and that, depending upon the particular conditions and specific catalyst and solvent chosen, there will be concomitant production of other products in variable amounts, particularly methanol. However, the conditions in the instant process are most preferably regulated so as to give high selectivity to the desired glycol aldehyde.

A suitable source of formaldehyde can be any one of those known in the art, including paraformaldehyde, methylal, formalin solutions, polyoxymethylenes and the like. Of these, paraformaldehyde is preferred and maximum yields have been obtained from its use.

While carbon monoxide and hydrogen react in a stoichiometric one-to-one ratio, it is not necessary to have them present in such a ratio to undertake the reaction. As indicated above, the reactant should be employed at a high enough pressure so as to provide a desirable reaction rate. Carbon monoxide also stabilizes rhodium and other transition metals to reduction by formaldehyde to the zero valent state. The carbon monoxide and hydrogen reactants may conveniently be supplied in about a one-to-one ratio, on a mole basis, such as can be obtained from synthesis gas and the like; however, they can also be present in widely varying and variable ranges, such as having mole ratios from about 5 to 95 to 95 to 5. Excellent yields can be obtained when operating at carbon monoxide to hydrogen partial pressure ratios as high as 10 to 1. Large excesses of hydrogen have a tendency to favor the production of unwanted methanol, while it is often desirable to have at least an equimolar amount of carbon monoxide present, particularly if temperature or other reaction conditions are such so as to present a need to suppress methanol production.

The catalyst can be prepared through a variety of techniques, e.g., the complex containing carbon monoxide can either be preformed or formed in situ by the reaction with the transition metal. Several convenient methods for in situ preparation are to contact a metal complex precursor with the phosphine-amide and an acid such as trifluoroacetic acid; to contact a metal carbonyl halide, e.g., [RhCl(CO)$_2$]$_2$ with the phosphine-amide; to contact a preformed metal coordination complex such as RhCl(CO) (PPh$_3$)$_2$ with the desired phosphine-amide; or to contact the metal carbonyl halide, e.g. [RhCl(CO)$_2$]$_2$ with a catalytic amount of base and the phosphine-amide.

Although it is not wished to be bound by theory, the reason for the selectivity of the formaldehyde hydroformylation to glycol aldehyde when using the transition metal-phosphine-amide in non-amide solvents is most likely to be found in the size and resulting stability of the formed chelate ring. Depending on the particular metal used, and, to a lesser extent, the particular phosphineamide ligand employed, a variety of desired bidentate complexes can be created, which complexes apparently bond with the transition metal at the phosphorous and the amide group oxygen. For example, the preferred phosphineamide ligands, N-methyl-N-octadecyl diphenylphosphino-propionamide, PPh$_2$CH$_2$CH$_2$C(O)N(CH$_3$)[(CH$_2$)$_{17}$CH$_3$] is believed to form a 6 membered ring with rhodium and is surprisingly active, as well as selective to glycol aldehyde.

A number of suitable non-lipophilic phosphine-amide ligands are exemplified below:

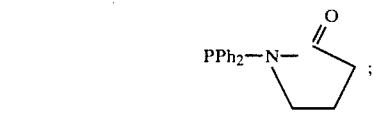

PPh$_2$OCH$_2$C(O)N(CH$_3$)$_2$;
PPh$_2$N(CH$_3$)CH$_2$C(O)N(CH$_3$)$_2$;

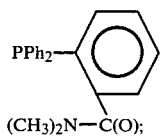

(CH$_3$)$_2$N—C(O);

PPh$_2$CH$_2$CH$_2$N(CH$_3$)C(O)CH$_3$;

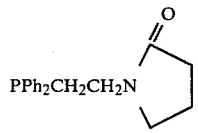

(5)

P(CH$_2$CH$_2$CH$_2$CH$_3$)$_2$[CH$_2$CH$_2$C(O)N(CH$_3$)$_2$]';
PPh$_2$CH$_2$CH$_2$C(O)N(CH$_3$)(CH$_2$CH$_2$CH$_2$CH$_2$CH$_2$CH$_2$CH$_3$);
PPh$_2$CH$_2$C(O)N(CH$_3$)$_2$; PPh$_2$CH$_2$N(CH$_3$)C(O)CH$_3$;
PPh$_2$CH$_2$CH$_2$C(O)N(CH$_3$)CH$_2$PPh$_2$;

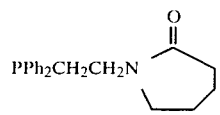

PPh$_2$CH$_2$CH$_2$C(O)N(CH$_2$Ph)(CH$_2$CH$_3$);
PPh$_2$CH$_2$CH$_2$C(O)N(Ph)(CH$_2$CH$_2$CH$_2$CH$_3$);

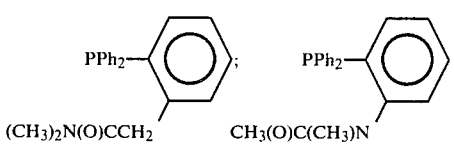

PPh$_2$CH$_2$C(O)N(Ph)$_2$.

A number of preferred suitable lipophilic phosphine-amside ligands are exemplified below:

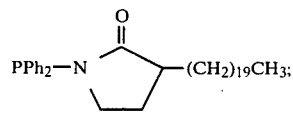

PPh$_2$OCH$_2$C(O)N(CH$_3$)(C$_{18}$H$_{37}$);
PPh$_2$N(CH$_3$)CH$_2$C(O)N(CH$_3$)(C$_{30}$H$_{61}$);

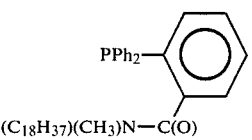

PPh$_2$CH$_2$CH$_2$N(C$_{10}$H$_{21}$)C(O)(C$_{10}$H$_{21}$);

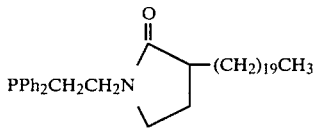

P(C$_4$H$_9$)$_2$[CH$_2$CH$_2$C(O)N(CH$_3$)(C$_{18}$H$_{37}$);
PPh$_2$CH$_2$CH$_2$C(O)N(CH$_3$)(C$_{50}$H$_{101}$);
PPh$_2$CH$_2$C(O)N(CH$_3$)(C$_{18}$H$_{37}$);
PPh$_2$CH$_2$N(C$_{10}$H$_{21}$)C(O)(C$_{20}$H$_{41}$);
PPh$_2$CH$_2$CH$_2$C(O)N(C$_{20}$H$_{41}$)(CH$_2$Ph);

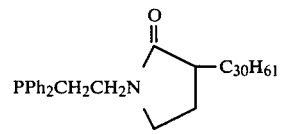

PPh$_2$CH$_2$CH$_2$C(O)N(CH$_2$Ph)(C$_{20}$H$_{41}$);
PPh$_2$CH$_2$CH$_2$C(O)N(Ph)(C$_{20}$H$_{41}$);

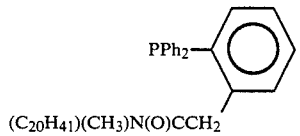

-continued

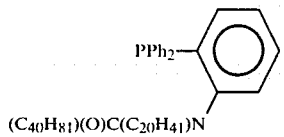

$(C_{40}H_{81})(O)C(C_{20}H_{41})N$ $PPh_2CH_2C(O)N(Ph)(C_{20}H_{41})$;
$PPh_2CH_2CH_2C(O)(C_{20}H_{41})(C_{10}H_{21})$.

The usage of this novel class of complexes as catalysts has surprisingly permitted the use of a great many more different solvents than have heretofore been found effective in such reactions. Although certain non-polar solvents, as well as mixtures, have proven to be operable, the use of polar solvents, and particularly organic polar solvents has been found to be generally preferred. Particularly preferred as solvents are nitriles, such as acetonitrile, benzonitrile, propionitrile and the like; cyclic ethers such as tetrahydrofuran, dioxane and tetrahydropyran; ethers such as diethyl ether, 1,2-dimethoxybenzene, alkyl ethers of alkylene glycols and polyalkylene glycols, e.g., methyl ethers of ethylene glycol, propylene glycol and di-, tri-, and tetraethylene glycols; alkyl sulfones and sulfoxides such as sulfolane and dimethylsulfoxide; ketones such as acetone, methyl isobutyl ketone, and cyclohexanone; esters such as ethyl acetate, ethyl propionate and methyl laurate; lactones of organic carboxylic acids such as butyrolactone and valerolactone, organic acids such as acetic acid, propionic acid and caproic acid, and alkanols, such as methanol, ethanol, propanol, 2-ethylhexanol and the like; as well as mixtures thereof. Non-polar organic solvents such as benzene, toluene and the like are also operable if used in mixtures with polar organics. The selected solvent should preferably be liquid under the reaction conditions.

The usage of the most preferred class of lipophilic complexes as catalysts has permitted the use of a solvent mixture which is both particularly adaptable for hydroformylation and also for product and catalyst separation. Suitable solvents for the most preferred embodiment of the process are selected from the class of organic polar, low boiling solvents and the class of organic non-polar, high boiling solvents, which combine to form a mixture containing at least one element of each group, and are disclosed in copending application Ser. No. 597,003, now U.S. Pat. No. 4,496,781. The preferred solvent mixture is an acetonitrile-xylenediethyl ether mixture.

A major factor to be considered in choosing a solvent, particularly for an industrial scale operation, is its suitability for subsequent product separation procedures. The use of non-amide solvents is particularly helpful in product separation procedures since their use disposes of having to separate the formed glycol aldehyde from the amide solvents in which aldol condensation and other competing side reactions occur. Other serious flaws of amide solvents are their tendency to form amines during the reaction process, and their high boiling points which can result in solvent decomposition during distillation. Amines, particularly tertiary amines, have been found to act as a poison in these reactions when present in suitable concentrations; as well as catalyzing aldol condensation, thus their presence is particularly undesirable. The only way in which amides can be separated from amine contamination is by distillation. Consequently, in any process system where maximum yields of glycol aldehyde are desired, it is a basic goal in the operation to avoid the presence of basic amines in any significant amount.

An additional improvement resulting from the catalyst complexes described herein is that in solution the phosphine-amides become bidentate ligands which are more resistant to displacement by glycol aldehyde than the prior art monodentate phosphines. This means that, in sharp contrast to prior art systems, the glycol aldehyde product does not have to be removed from the reaction media shortly after its formation so as to insure the stability of the catalyst. Such properties are extremely helpful in optimizing product yield and facilitating product and catalyst separation. The reaction can also be carried out at higher concentrations of formaldehyde without any harmful side reactions.

As in other processes of this kind, the reaction can be conducted in either a batch, semi-continuous or continuous mode of operation. It is naturally desirable to construct the reactor from materials which can withstand the operating temperatures and pressures required, while keeping the internal surfaces of the reactor substantially inert. Standard equipment known to permit control of the reaction, such as heat exchangers and the like, may be used. The reactor should be provided with an adequate means for agitating the reaction mixture; such mixing can be induced by vibration, shaking, stirring, oscillation, and similar type methods.

The reaction resulting in the production of glycol aldehyde, together with lesser amounts of methanol, is usually complete within a period of about 2-3 hours, although reaction time is not a critical parameter of the process, and longer or shorter times can be effectively employed. Substantially higher concentrations of reactants than previously utilized are preferred, and the reaction also yields higher selectivities of reactants than the prior art.

The amount of catalyst employed in the hydroformylation reaction process has not been found to be critical and can vary considerably. At least a catalytically effective amount of catalyst should be present, and preferably a sufficient amount of catalyst which is effective to provide a reasonable reaction rate. As little as $10^{-5}$ moles of catalyst per liter of reaction medium can suffice, while amounts in excess of $10^{-1}$ moles do not appear to materially affect the rate of reaction. For most purposes, an effective preferred amount of catalyst falls in the range of from about $10^{-2}$ to about $10^{-3}$ moles per liter.

The precise reaction conditions chosen are not particularly critical in that a wide range of elevated temperatures and superatmospheric pressures are operable. Using current available apparatus, the preferred temperature range should be at least about 50° C. and can range up to about 150° C. and even higher, although no substantial benefits are realized at this temperature level. Most preferably, the operating temperatures will range from about 90° C. to about 130° C. The superatmospheric pressures should be at least about 70 atmospheres and can range, in theory, to almost any pressure attainable with available production apparatus. Most preferably, operating pressures should fall in the range of about 140 to about 280 atmospheres, particularly when operating in the preferred aforementioned temperature range.

The following examples are provided to illustrate the invention in accordance with the principles of this invention but are not construed as limiting the invention in any way except as indicated by the appended claims. In the examples, selectivity is defined as mmoles of product divided by mmoles of reacted formaldehyde times 100.

EXAMPLES

The phosphine-amides were prepared by the following general methods:

Preparation of
N,N-dimethyl-3-diphenylphosphinopropionamide
[PPh$_2$CH$_2$CH$_2$C(O)N(CH$_3$)$_2$]

A 100 ml 3-necked round bottomed flash was preheated to 100° C. under a nitrogen atmosphere and 7.14 g diphenylphosphine (38.4 mmole) from Alfa, 0.15 g 2,2′-azobis (2-methylpropionitrile) from Aldrich, and 3.78 g dimethylacrylamide (38.2 mmole) from Polysciences were added in the stated sequence. The reaction mixture was maintained at 100° C. under a nitrogen atmosphere for 45 minutes and then evacuated (1 mm) for 24 hours at 100° C. The resulting oil was then cooled in the refrigerator for several hours until it solidified to a white solid. It was then washed with a 9:1 pentane:toluene mixture so as to free the excess diphenylphosphine.

The infrared spectra disclosed a strong γ(CO) band at 1650 cm$^{-1}$. The $^1$H NMR showed a multiplet at 2.2–2.5δ with a relative area of 4 assigned to the CH$_2$CH$_2$C(O) group; a doublet at 2.8δ (3 Hz) of relative area 6 assigned to the N(CH$_3$)$_2$ group; and a multiplet at 7.1–8.3δ of relative area of 10 assigned to the P(C$_6$H$_5$)$_2$ group.

The elemental analysis was the following: calculated (found); C, 71.58 (70.95); H, 7.02 (7.03); N, 4.91 (4.05); P, 10.87 (10.75). Product Yield was 71%.

Preparation of
N-methyl-N-(2-diphenylphosphinoethyl) acetamide
[PPh$_2$CH$_2$CH$_2$N(CH$_3$)C(O)CH$_3$]

A 100 ml 3-necked round bottomed flash was heated to 100° C. under a nitrogen atmosohere and 7.14 g diohenylphosphine (38.4 mmole), 0.15 g 2,2′-azobis (2-methyloropionitrile), and 3.77 g N-vinyl-N-methyl acetamide (38.1 mmole) from Polysciences were added in the stated sequence. The reaction was maintained at 100° C. for 45 minutes under a nitrogen atmosphere and then evacuated (1 mm) for 24 hours at 100° C. A viscuous oil resulted whose infrared spectrum disolayed a strong γ(CO) band at 1645 cm$^{-1}$ and a small γ(P—H) band at 2300 cm$^{-1}$ due to a small amount of diphenylphosphine impurity. The elemental analysis was the following: calculated (found); C, 71.58 (69.89); H, 7.02 (7.15); N, 4.91 (4.57); P, 10.87 (10.97). The yield was 94%.

Preparation of
N-(-2-diphenylohosphinoethyl)-2-pyrrolidinone

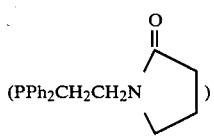

The cited phosphine-amide was prepared in a similar manner to the earlier two examples by using 14.28 g diphenylphosphine (76.8 mmole), 0.30 g 2,2′-azobis (2-methylpropionitrile) and 8.52 g N-vinyl-2-pyrrolidinone (76.8 mmole) from Aldrich. The reactants added in the stated sequence were stirred at 100° C. for 0.5 hours under a nitrogen atmosphere followed by evacuation (1 mm) for 24 hours. The yield was 96%.

The infrared spectrum disclosed a strong, broad γ(CO) band at 1680 cm$^{-1}$ and a small absorption at 2310 cm$^{-1}$ due to a small amount of γ(P—H) impurity. The elemental analysis was the following: calculated (found); C, 72.70 (72.68); H, 6.79 (6.73); N, 4.70 (3.49); P, 10.42 (11.60). The $^1$H NMR showed a multiplet at 1.6–2.6δ with a relative area of 6 assigned at —CH$_2$CH$_2$C(O)— and P—CH$_2$— groups, a multiplet at 3.2–3.8δ with a relative area of 4 assiqned to the two CH$_2$—N-groups and a multiplet at 7.2–8.0δ with a relative area of 11 assigned to the P(C$_6$H$_5$)$_2$ group. A small amount of diphenylphosphine impurity accounts for this slightly greater area for the phenyl region. The disappearance of the multiplet signals of the vinyl protons at 6.9–7.4δ and 4.3–4.7δ confirms the complete disappearance of N-vinylpyrrolidinone.

The following examples illustrate a direct comparison between the phosphine-amides of this invention with triphenylphosphine and in one case ethyldiphenylphosphine (another alkyldiphenylphosphine) in various solvents.

The following examples are provided to illustrate the invention in accordance with the principles of this invention but are not construed as limiting the invention in any way except as indicated by the appended claims.

EXAMPLE 1

A 300 cc stainless steel autoclave equipped with a stirrer, thermocouple, and cooling coil was charged with 100 g acetonitrile, 3.0 g of 95% paraformaldehyde (95 mmole of equivalent formaldehyde), 0.081 g chlorodicarbonylrhodium (I) dimer (0.208 mmole) and 0.364 g N,N-dimethyl-3-diphenylphosphinopropionamide (1.28 mmole), which was sparged with dry nitrogen. The autoclave was sealed and the air was further removed by flushing the autoclave three times with a 1:1 mixture of carbon monoxide; hydrogen at 100 psi. The autoclave was then charged with 1500 psi of the carbon monoxide: hydrogen mixture. The autoclave and its liquid contents were next heated to 130° C. and the final pressure registered 1900 psi. After three hours, the autoclave was cooled to room temperature and the gas was vented. Gas chromatography and high pressure liquid chromatography of the resulting liquid phase disclosed 37 mmole of formaldehyde remaining (61% conversion) with 35 mmole glycol aldehyde (60% selectivity) and 4.1 mmole of methanol (7.1% selectivity). The selectivity is defined as mmoles of product divided by mmoles of reacted formaldehyde times 100 in all examples.

COMPARATIVE EXAMPLE 1

An equimolar concentration of triphenylphosohine was substituted for N,N-dimethyl-3-diphenylphosphinopropionamide, under the identical conditions of Example 1. Analysis of the liquid phase showed 53 mmole of formaldehyde remaining (44% conversion), with 7.6 mmole of glycol aldehyde and 0.8 mmole of ethylene glycol (20% selectivity) and 8.0 mmole of methanol (19% selectivity).

SECOND COMPARATIVE EXAMPLE 1

An equimolar concentration of ethyldiphenylphosphine was substituted for N,N-dimethyl-3-diphenylphosphinopropionamide, under the identical conditions of Example 1. Analysis of the liquid phase showed 5.5 mmole formaldehyde remaining (94% conversion) with 0.6 mmole glycol aldehyde (0.7% selectivity) and 1.6 mmole methanol (1.8% selectivity).

EXAMPLE 2

A 125 cc stainless steel Parr bomb equipped with a glass liner and a magnetic stirrer was charged with 25.0 g acetonitrile, 0.75 g paraformaldehyde (23.8 mmole), 0.020 g chlorodicarbonylrhodium (I) dimer (0.058 mmole) and 0.090 g N,N-dimethyl-3-diphenylphosphinopropionamide (0.348 mmole) which had been sparged with nitrogen. The bomb was then charged with 1500 psi of a 1:1 carbon monoxide: hydrogen mixture, heated to 130° C. for 3.0 hours, and then cooled to room temperature and vented. Analysis of the liquid contents indicated 9.3 mmole formaldehyde remaining 61% conversion), 11.9 mmole glycol aldehyde (82% selectivity), and 0.2 mmole methanol (1.4% selectivity).

COMPARATIVE EXAMPLE 2

The bomb used in Example 2 was charged and reacted under identical conditions to those of Example 2 except the catalyst was chlorocarbonylbis (triphenylphosphine) rhodium (I) (0.080 g, 0.116 mmole) in the absence of N,N-dimethyl-3-diphenylphosphinopropionamide as co-catalyst. Analysis of the liquid contents indicated 3.8 mmole formaldehyde remaining (84% conversion), 0.5 mmole glycol aldehyde (3% selectivity), and 0.4 mmole methanol (2% selectivity).

EXAMPLE 3

The Parr bomb used in Example 2 was charged with 25.0 g acetonitrile, 0.75 g paraformaldehyde (23.8 mmole), 0.080 g chlorocarbonylbis(triphenylphosphine)rhodium (I) (0.116 mmole), and 0.060 g N,N-dimethyl-3-diphenylphosphinopropionamide (0.232 mmole) which had been sparged with nitrogen. The bomb was then charged with 1500 psi of a 1:1 carbon monoxide:hydrogen mixture at room temperature and subsequently heated to 130° C. for 3.0 hours. After cooling and gas venting, the analysis indicated 7.6 mmoles of formaldehyde remaining (68% conversion), 11.1 mmoles glycol aldehyde (69% selectivity), and 5.0 mmoles methanol (31% selectivity).

EXAMPLE 4

The Parr bomb used in Example 2 was run under identical conditions to Example 2 except that an equimolar concentration of N-methyl-N-(2-diphenylphosphinoethyl) acetamide was substituted for N,N-dimethyl-3-diphenylphosphinopropionamide. Analysis of the liquid contents indicated 13.4 mmole formaldehyde remaining (44% conversion), 5.3 mmole glycol aldehyde (51% selectivity), and 2.1 mmole methanol (20% selectivity).

EXAMPLE 5

The autoclave used in Example 1 was charged with 9.0 g paraformaldehyde (285 mmole), 65.0 g acetonitrile, 30.0 g toluene, 5.0 g diethyl ether, 0.301 g N,N-dimethyl-3-diphenylphosphinopropionamide (1.06 mmole), and 0.069 g chlorodicarbonylrhodium (I) dimer (0.178 mmole). The autoclave was charged with 1750 psi carbon monoxide and 450 psi hydrogen at room temperature. A 2 liter autoclave reservoir was also charged with this same carbon monoxide:hydrogen ratio and heated to 250° C. to a total pressure of 3600 psi. The reactor autoclave was heated to 130° C. for 3.0 hours to a total pressure of 3600 psi. When the gas uptake lowered the gas pressure to 3200 psi, gas was transferred from the reservoir autoclave to the reactor autoclave during the run. Upon completion, the autoclave was cooled to room temperature and slowly vented. Analysis of the liquid products revealed 136 mmole formaldehyde remaining (52% conversion), 120 mmole glycol aldehyde (81% selectivity) and 12.9 mmole methanol (8.7% selectivity).

COMPARATIVE EXAMPLE 5

A comparative example, using an equimolar quantity of triphenylphosphine instead of N,N-dimethyl-3-diphenylphosphinopropionamide under identical conditions, resulted in a liquid phase containing 174 mmole formaldehyde remaining (39% conversion), with 27.3 mmole glycol aldehyde (25% selectivity) and 25.2 mmole methanol (23% selectivity).

EXAMPLE 6

The autoclave in Example 5 was charged with 9.0 g paraformaldehyde (285 mmole), 65.0 g acetonitrile, 30.0 g toluene, 5.0 g diethyl ether, 0.315 g N(-2-diphenylphosphinoethyl)-2-pyrrolidinone (1.06 mmole), and 0.069 g chlorodicarbonylrhodium (I) dimer (0.178 mmole). The autoclave was then charged with 1750 psi carbon and 450 psi hydrogen at room temperature. The 2 liter autoclave reservoir was also used, as in Example 5. The reactor sutoclave was heated to 130° C. for 3.0 hours. Analysis of the liquid products revealed 137 mmole formaldehyde remaining (52% conversion), 143 mmole glycol aldehyde (97% selectivity) and 3.6 mmole methanol (2% selectivity).

EXAMPLE 7

The autoclave of Example 5 was charged with 100 g tetraglyme, 9.0 g paraformaldehyde (285 mmole), 0.069 g chlorodicarbonylrhodium (I) dimer (0.177 mole), and 0.301 g N,N-dimethyl-3-diphenylphosphinopropionamide (1.06 mmole). The gas reservoir of Example 5 was again used in the same manner. The autoclave was charged with 1750 psi carbon monoxide and 450 psi hydrogen at room temperature and then heated to 130° C. for 3.0 hours to a total pressure of 3600 psi. The autoclave was cooled, vented, and the liquid contents analyzed as 104 mmole formaldehyde remaining (64% conversion), 111 mmole glycol aldehyde and 1.2 mmole ethylene glycol (62% selectivity), and 14.6 mmole methanol (8.1% selectivity).

COMPARATIVE EXAMPLE 7

A comparative example using an equimolar concentration of triphenylphosphine instead of N,N-dimethyl3-diphenylphosphinopropionamide under identical conditions resulted in a liquid phase containing 75 mmole formaldehyde remaining (74% conversion), 7.6 mmole glycol aldehyde (3.6% selectivity), and 5.1 mmole methanol (2.4% selectivity).

EXAMPLE 8

The autoclave and reservoir of Example 5 were again run under identical conditions and the charge was identical except that 100 g acetone was used as the solvent. Analysis of the liquid contents indicated 106 mmole of formaldehyde remaining (63% conversion), with 145 mmole of glycol aldehyde (81% selectivity) and 10.2 mmole methanol (5.7% selectivity).

COMPARATIVE EXAMPLE 8

A comparative example using an equimolar concentration of triphenylphosphine instead of N,N-dimethyl-3-diphenylphosphinopropionamide under identical conditions produced a liquid phase containing 164 mmole of formaldehyde remaining (42% conversion) with 30.9 mmole glycol aldehyde (26% selectivity) and 11.2 mmole methanol (9.2% selectivity).

EXAMPLE 9

The 125 cc stainless steel Parr bomb used in Example 2 was charged with 25.0 g sulfolane, 0.75 g paraformaldehyde (23.8 mmole), 0.082 g chlorocarbonylbis (triphenylphosphine)rhodium(I) (0.118 mmole) and 0.061 g N,N-dimethyl-3-diphenylphosphinopropionamide (0.213 mmole) which had been sparged with nitrogen. The bomb was then charged with 1600 psi of a 1:1 carbon monoxide: hydrogen gas mixture and subsequently heated to 130° C. for 3.0 hours. The bomb was then cooled to room temperature, the gases vented, and the liquid contents analyzed as 10.8 mmole formaldehyde remaining (55% conv.), 9.1 mmole glycol aldehyde (70% selectivity) and 5.4 mmole methanol (42% selectivity).

COMPARATIVE EXAMPLE 9

A comparative example run under identical conditions as those of example 9 except no N,N-dimethyl-3-diphenylphosphinopropionamide was used. The analysis of the liquid phase gave 3.8 mmole formaldehyde remaining (84% conversion), 1.75 mmole glycol aldehyde (8.8% selectivity) and 1.63 mmole methanol (8.2% selectivity).

EXAMPLE 10

The 300 cc stainless steel autoclave used in Example 1 was charged with 100 g acetonitrile, 3.0 g paraformaldehyde (95 mmole), 0.121 g dicarbonylacetylacetonato rhodium (I) (0.469 mmole), 0.054 g trifluoroacetic acid (0.473 mmole), and 0.362 g N,N-dimethyl-3-diphenylphosphinopropionamide (1.27 mmole). The autoclave was then charged with 1750 psi carbon monoxide and 450 psi hydrogen at room temperature and heated to 110° C. for 2 hours, whereupon the reactor was cooled and vented. The liquid contents were analyzed for 13.3 mmole formaldehyde remaining (86% conversion), 74 mmole glycol aldehyde and 1.2 mmole ethylene glycol (92% selectivity) and 3.4 mmole methanol (4.2% selectivity).

COMPARATIVE EXAMPLE 10

A comparative example under identical conditions using an equimolar concentration of triphenylphosphine rather than N,N-dimethyl-3-diphenylphosphinopropionamide resulted in a liquid phase containing 49.3 mmole glycol aldehyde (72% selectivity), 3.9 mmole methanol (5.6% selectivity) and 25.4 mmole formaldehyde remaining (73% conversion).

EXAMPLE 11

The 300 cc stainless steel autoclave equipped as in Example 1 was charged with 100 g tetraglyme, 3.0 g of 95% paraformaldehyde (95 mmole), 0.121 g dicarbonylacetoacetonato rhodium (I) (0.469 mmole), 0.054 g trifluoroacetic acid (0.470 mmole) and 0.362 g N,N-dimethyl3-diphenylphosphinopropionamide (1.27 mmole) after a nitrogen sparge of the solution. The autoclave was sealed and flushed several times with 100 psi carbon monoxide. The autoclave was then charged with 1750 psi of carbon monoxide and 450 psi hydrogen at room temperature. The autoclave and its contents were heated to 110° C. and an initial pressure of 3600 psi. A heated gas reservoir containing the same carbon monoxide:hydrogen ratio as the autoclave was used to charge the reaction autoclave when gas absorption lowered the autoclave pressure below 3200 psi. After three hours of reaction, the autoclave was cooled and vented. Analysis indicated 24.4 mmole formaldehyde remaining (74% conversion), 38.5 mmoles glycol aldehyde and 1.7 mmole ethylene glycol (57% selectivity) and 20.9 mmoles methanol (30% selectivity).

COMPARATIVE EXAMPLE 11

A comparative example under identical conditions with an equimolar concentration of triphenylphosphone instead of N,N-dimethyl-3-diphenylphosphinopropionamide resulted in a liquid phase having 24.4 mmole formaldehyde remaining (74% conversion), 22.0 mmole glycol aldehyde and 1.5 mmole ethylene glycol (33% selectivity), and 24.1 mmole methanol (34% selectivity).

EXAMPLE 12

The stainless steel autoclave equipped as in Example 1 was charged with 100 g acetonitrile, 3.0 g paraformaldehyde (95 mmole), 0.090 g chlorodicarbonyl rhodium (I) dimer (0.232 mmole), 0.057 g 4-dimethylaminopyridine (0.464 mmole), and 0.397 g N,N-dimethyl-3-diosphinopropionamide (1.39 mmole) which had been sparged with nitrogen. The autoclave was charged with 1750 psi carbon monoxide and 450 psi hydrogen at room temperature and the autoclave and its contents were then heated to 110° C. for three hours. A gas reservoir was used to keep the pressure above 3200 psi, as in Example 10. Analysis indicated 5.5 mmole formaldehyde remaining (94% conversion), 64.5 mmole glycol aldehyde and 1.8 mmole ethylene glycol (74% selectivity), and 7.1 mmole methanol (7.9% selectivity).

EXAMPLE 13

The 300 cc stainless steel autoclave equipped as in Example 1 was charged with 100 g acetonitrile, 9.0 g paraformaldehyde (285 mmole), 0.090 g chlorodicarbonylrhodium (I) dimer (0.232 mmole), 0.114 g 4-dimethylaminopyridine (0.930 mmole), and 0.397 g N,N-dimethyl-3-diphenylphosphinopropionamide. The autoclave was charged with 1500 psi carbon monoxide and 450 psi hydrogen at room temperature and then heated to 100° C. for one hour. A gas reservoir having the same carbon monoxide to hydrogen ratio as the autoclave was used to keep the gas pressure above 3200 psi. Upon completion, the autoclave was cooled and the gas vented. Analysis of the liquid solution indicated 89 mmole of formaldehyde remaining (69% conversion), 155 mmole glycol aldehyde and 1.6 mmole ethylene glycol (80% selectivity) and 21.5 mmole methanol (11% selectivity).

Cobalt and ruthenium were also active for formaldehyde hydroformylation, although less active than rhodium, as is shown in the following examples.

EXAMPLE 14

The 300 cc stainless steel autoclave used in Example 1 was charged with 6.0 g paraformaldehyde (190 mmole, 100 g acetonitrile, 0.314 g ruthenium carbonyl (0.491 mmole), and 0.855 g N,N-dimethyl-3-diphenylphosphinopropionamide (3.00 mmole). The autoclave was sealed and charged with 1400 psi carbon monoxide and 1350 psi hydrogen at room temperature and then heated to 130° C. for 2.0 hours. After cooling and venting, the analysis indicated 57.6 mmole formaldehyde remaining ( 70% conversion), 6.2 mmole glycol aldehyde and 4.1 mmole ethylene glycol (7.8% selectivity), and 5.3 mmole methanol (4.0% selectivity).

EXAMPLE 15

The 100 cc Parr bomb equipped as in Example 2 was charged with 25 g acetonitrile, 0.75 g paraformaldehyde (23.8 mmole), 0.240 g dicobalt octacarbonyl (0.696 mmole), and 0.401 g N,N-dimethyl-3-diphenylphosphinopropionamide (1.39 mmole). The bomb was sealed and flushed twice with a 1:1 carbon monoxide:hydrogen mixture. The bomb was then charged with 1500 psi of the gas mixture, whereupon the autoclave and its contents were heated to 130° C. for 3.0 hours, cooled to room temperature and vented. The liquid contents were analyzed as 7.21 mmoles formaldehyde remaining (69% conversion), 2.92 mmoles glycol aldehyde (18% selectivity) and 0.08 mmoles methanol (0.5% selectivity).

Preparation of
N-methyl-N-octadecyl-3-diphenylphosphinopropionamide [$PPh_2CH_2CH_2C(O)N(CH_3)(C_{18}H_{37})$]

A mixture of 5.7 g ethyl-3-diphenylphosphinopropionate (19.9 mmoles), 5.1 g N-methyl-n-octadecylamine (18.0 mmoles), and 0.3 g sodium methoxide (5.6 mmoles) were first deoxygenated and then heated to 100° C. under a nitrogen atmosphere for 24 hours. The mixture was then cooled and extracted with pentane. The pentane soluble was rotovapped to an oil.

Infrared analysis displayed a strong, broad $\gamma(CO)$ band at 1650 cm$^{-1}$. The elemental analysis was the following: calculated (found); C, 77.94 (76.98); H, 10.42 (9.83); P, 5.92 (6.00); N, 2.67 (2.66). The $^1$H NMR showed a multiplet at 2.3–2.5$\delta$ with a relative area of 4 assigned to the $CH_2CH_2C(O)$ group, a multiplet at 2.9–3.4$\delta$ with a relative area of 5 assigned to the $N(CH_3)(CH_2)$-group, a multiplet at 0.8–1.8$\delta$ of relative area 35 assigned to the $C_{17}H_{35}$ alkyl chain, and a multiplet at 7.1–7.8$\delta$ of relative area of 10 assigned to the $P(C_6H_5)_2$ group.

EXAMPLE 16

A 300 cc stainless steel autoclave equipped with a stirrer, thermocouple, and cooling coil was charged with 65 g acetonitrile, 30 g m-xylene, 5 g diethyl ether, 9.0 g of 95% paraformaldehyde (285 mmole of equivalent formaldehyde), 0.121 dicarbonylacetylacetonato rhodium (I) (0.469 mmole), 0.055 g trifluoroacetic acid (0.482 mmole), and 0.782 g N-methyl-N-octadecyl-3-diphenylphosphinopropionamide (1.39 mmole) which had been sparged with dry nitrogen. The autoclave was sealed and the air was further removed by flushing the autoclave three times with carbon monoxide at 100 psi. The autoclave was then charged with 1750 psi carbon monoxide and 450 psi hydrogen at room temperature. A 2-liter autoclave reservoir was also charged with these same gas pressures and heated to 270° C. to a total pressure of 3900 psi. The reactor autoclave was heated to 110° C. for 3.0 hours to a total pressure of 3800 psi. When gas uptake lowered the pressure to 3600 psi, gas was transferred from the reservoir autoclave to the reactor autoclave during the run. Analysis of the liquid products by gas chromotography and high pressure liquid chromotography revealed 104 mmole formaldehyde remaining (64% conversion), 165 mmole glycol aldehyde and 4 mmole ethylene glycol (93% selectivity), 6 mmole glyceraldehyde (3% selectivity), and 6 mmole methanol (3% selectivity).

The glycol products and remaining formaldehyde were separated from the rhodium catalyst by first distilling the volatiles (acetonitrile, diethyl ether, trifluoroacetic acid) with a 5 plate ⅜" diameter Oldershaw column at a 1:1 reflux ratio with 180 mm Hg pressure under a carbon monoxide sparge at 45°–60° C. The glycol aldehyde and remaining formaldehyde precipitated into a separate oily layer when the volatiles were removed. The orange rhodium catalyst remained in the m-xylene layer which was decanted. The last traces of m-xylene in the glycol aldehyde were washed with 5 g of diethyl ether which was separated from the other volatiles in a subsequent step. The similar densities of m-xylene and glycol aldehyde makes this necessary. Rhodium analysis of the glycol aldehyde layer showed 86 ppm Rh. The excess formaldehyde was distilled to give pure glycol aldehyde.

First Recycle

The combined m-xylene and diethyl ether with the soluble rhodium catalyst from the first cycle were again combined with 9.0 g 95% paraformaldehyde, 0.055 g (0.482 mmole) trifluoroacetic acid, 65 g acetonitrile, charged into the autoclave, and reacted at 110° C. for 3.0 hours as before. Analysis of the liquid products revealed 140 mmole of formaldehyde remaining (51% conversion) with 142 mmole of glycol aldehyde and 2 mmole of ethylene glycol (99% selectivity), and 1 mmole of methanol (1% selectivity). The volatile acetonitrile and diethyl ether were distilled off as before to precipitate the glycol aldehyde and remaining formaldehyde. The rhodium catalyst remained in the m-xylene layer. The glycol aldehyde layer was washed with diethyl ether as before and finally it was combined with the m-xylene. Atomic absorption indicated 95 ppm rhodium in the glycol aldehyde layer.

Second Cycle

The recycled m-xylene and diethyl ether with the soluble rhodium catalyst were again combined with 9.0 g 95% paraformaldehyde (285 mmole), 0.055 g trifluoroacetic acid (0.482 mmole), 65 g acetonitrile and reacted in the same way as before. Analysis of a liquid sample indicated 131 mmole of formaldehyde remaining (54% conversion) with 145 mmole of glycol aldehyde and 2.8 mmole of ethylene glycol (96% selectivity), and 3.1 mmole of methanol (20% selectivity). The volatiles were distilled in the same way precipitating glycol aldehyde which was washed with purified diethyl ether as before to wash out the last remaining rhodium entrained in the glycol aldehyde. Analysis of the glycol aldehyde layer by atomic absorption indicated 34 ppm rhodium.

Third Cycle

The m-xylene-diethyl ether solvent mixture with the rhodium catalyst was again combined with 0.054 g trifluoroacetic acid (0.474 mmoles), 9.0 g 95% paraformaldehyde (285 mmole equivalent formaldehyde), 65 g acetonitrile and charged into the autoclave at the above conditions. Analysis of the liquid products revealed 154 mmole of formaldehyde remaining (46% conversion), 127 mmole of glycol aldehyde and 2.3 mmole of ethylene glycol (99% selectivity) and no detectable methanol. Analysis of the glycol aldehyde layer by atomic absorption after catalyst separation as above indicated 64 ppm rhodium.

Fourth Recycle

The recovered rhodium catalyst in the m-xylenediethyl ether solvent mixture was again combined with 0.055 trifluoroacetic acid (0.482 mmole), 9.0 g 95% paraformaldehyde, (285 mmole), 65 g acetonitrile and charged into the autoclave under the above conditions. Analysis of the liquid products after reaction revealed 170 mmole of formaldehyde remaining (40% conversion), 101 mmole of glycol aldehyde (88% selectivity) and no detectable methanol. The glycol aldehyde was separated from the rhodium catalyst as before and 96 ppm rhodium was measured in the glycol aldehyde by atomic absorption. In principle the catalyst could be recycled many more times in the same manner.

COMPARATIVE EXAMPLE 16

The 300 cc stainless steel autoclave was charoed with 65 g acetonitrile, 30 g m-xylene, 5 g diethyl ether, 9.0 g 95% paraformaldehyde (285 mmole of equivalent formaldehyde), 0.121 g dicarbonylacetylacetonato rhodium (I) (0.469 mmole), 0.054 g trifluoroacetic acid (0.474 mmole), and 0.397 g N,N-dimethyl-3-diphenylphosphinopropionamide (1.39 mmole) which had been sparged with dry nitrogen. The autoclave was sealed and the reaction was carried out under identical conditions to Example 1. Analysis of the liquid products by gas chromatography and high pressure liquid chromatography revealed 59 mmole of formaldehyde (79% conversion), 185 mmole of glycol aldehyde and 2 mmole of ethylene glycol (83% selectivity), 8 mmole of glyceraldehyde (4% selectivity), and 8 mmole of methanol (4% selectivity).

The glycol products and formaldehyde were separated from the rhodium catalyst by first distilling the volatiles with a 5 plate ⅜" diameter Oldershaw column at a 1:1 reflux ratio with 180 mm Hg pressure under a carbon monoxide sparge at 45°–60° C. The glycol aldehyde and remaining formaldehyde precipitated when the volatiles were removed. Both the m-xylene and the oily layer of glycol aldehyde and unreacted formaldehyde were red in color. Determination of rhodium in the glycol aldehyde layer revealed 2100 ppm rhodium by atomic absorption.

First Recycle

The m-xylene solution with rhodium catalyst was combined with 5 g diethyl ether, 65 g acetonitrile, and 9.0 g 95% paraformaldehyde (285 mmole equivalent formaldehyde) and charged into the 300 cc autoclave as before. It was reacted under identical conditions to the first cycle. After cooling, the analysis of the liquid products revealed 182 mmole formaldehyde left (36% conversion) with 70 mmole of glycol aldehyde (68% selectivity) and 20 mmole methanol (19% selectivity). Only 180 psi Rh (measured by atomic absorption) was still in the liquid solution.

Other rhodium catalyst precursors could be recycled in a similar manner with the lipophilic phosphine co-catalyst.

EXAMPLE 17

The 300 cc stainless steel autoclave in Example 1 was charged with 65 g acetonitrile, 30 g m-xylene, 5 g diethyl ether, 9.0 g 95% paraformaldehyde (285 mmole of equivalent formaldehyde), 0.092 g chlorodicarbonylrhodium (I) dimer (0.24 mmole) and 0.737 g N-methyl-N-octadecyl3-diphenyl phosphinopropionamide (1.41 mmole) which had been sparged with dry nitrogen. The autoclave was sealed and flushed three times with carbon monoxide at 100 psi. The autoclave was then charged with 1750 psi carbon monoxide and 450 psi hydrogen at room temperature. The reactor autoclave was heated to 120° C. for 3.0 hours to a total pressure of 3600 psi. When gas uptake lowered the pressure to 3300 psi, gas was transferred from a reservoir autoclave to the reactor autoclave. After the reactor was cooled and vented, analyses of the liquid products by gas and high pressure liquid chromotography revealed 58 mmole of formaldehyde (80% conversion), 152 mmole of glycol aldehyde and 4 mmole of ethylene glycol (69% selectivity), 18 mmole of glyceraldehyde (8% selectivity), and 31 mmole of methanol (14% selectivity).

The glycol products and remaining formaldehyde were separated from the rhodium catalyst by first distilling the volatiles (acetonitrile, diethyl ether, trifluoroacetic acid, methanol) as in Example 1. The glyceraldehyde, glycol aldehyde and remaining formaldehyde separated into a separate oily phase when the volatiles had been removed. The m-xylene solution in which the rhodium catalyst was dissolved was decanted. Atomic absorption of the glycol aldehyde mixture revealed 24 ppm rhodium.

First Recycle

The m-xylene solvent mixture with the rhodium catalyst from the first cycle was combined with 9.0 g 95% paraformaldehyde (285 mmoles), 5 g diethyl ether, 65 g acetonitrile, and reacted at 120° C. for 3.0 hours as before.

After cooling and venting, analysis of the liquid products revealed 116 mmole formaldehyde remaining (59% conversion), 122 mmole glycol aldehyde and 2 mmole ethylene glycol (73% selectivity), 10 mmole glyceraldehyde (6% selectivity), and 15 mmole methanol (9% selectivity). The volatiles were removed to separate the m-xylene layer containing the soluble rhodium catalyst from the organic reactants and products. Atomic absorption of the glycol aldehyde layer revealed 12 ppm rhodium.

Second Recycle

The m-xylene with the rhodium catalyst was combined with 5 g diethyl ether, 65 g acetonitrile, and 9.0 g paraformaldehyde (285 mmole formaldehyde). The mixture was purged with nitrogen, charged into the autoclave in Example 1, and reacted at 120° C. for 3.0 hours under the same carbon monoxide-hydrogen pressures as before. The vessel was cooled, vented, and the volatiles removed as before. Analysis of the liquid phase revealed 122 mmole of formaldehyde remaining (57% conversion) with 107 mmole glycol aldehyde and 1 mmole ethylene glycol (66% selectivity), 5 mmole glyceraldehyde (3% selectivity), and 4 mmole methanol (2% selectivity). Atomic absorption of the glycol aldehyde layer revealed 66 ppm rhodium. The remainer was in the m-xylene phase as before.

Third Recycle

The m-xylene with the rhodium catalyst was combined with 5 g diethyl ether, 65 g acetonitrile, and 9.0 g paraformaldehyde (285 mmole). It was again charged into the autoclave in Example 1 and reacted at 120° C. under the same pressure of carbon monoxide-hydrogen for 3.0 hours. Analysis of the liquid products revealed 140 mmole for formaldehyde remaining (51% conversion), 84 mmole of glycol aldehyde (58% selectivity), 1 mmole of glyceraldehyde (1% selectivity), and 1 mmole of methanol (1% selectivity).

In principle, the same technique could be used to recycle the rhodium catalyst many times.

I claim:

1. A process for the preparation of glycol aldehyde comprising contacting formaldehyde, carbon monoxide and hydrogen in the presence of an effective polar or, non-polar organic solvent and metal catalyst complex, under superatmospheric pressures and elevated temperatures; the metal catalyst complex having the formula:

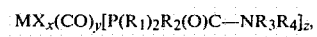

$$MX_x(CO)_y[P(R_1)_2R_2(O)C-NR_3R_4]_z,$$

wherein M is a metal selected from the group of rhodium, cobalt, ruthenium and mixtures thereof;

X is an anion selected from the class of halides, pseudohalides, hydrides, and deprotonated strong carboxylic acids;

P is phosphorous;

$R_1$ is an aliphatic or aromatic group containing from 1-20 carbon atoms;

$R_2$ is an aliphatic or aromatic group containing from 0-20 carbon atoms, which group is either unsubstituted, or substituted with oxygen, nitrogen and sulfur atoms which are either directly bonded to the amide C(O)N carbon or nitrogen or, to an $R_2$ carbon atom; if $R_2=0$, then the phosphorous atom is directly bonded to the amide nitrogen;

$R_3$ and $R_4$ are aliphatic or aromatic groups containing from 1-100 carbon atoms;

x ranges from 0 to 3, y ranges from 1 to 5, and z from 1 to 4;

the resultant compound further characterized by the absence of hydrogen on the amido nitrogen atom and the additional limitation that if $R_2$ is bonded to the amide nitrogen, then either $R_3$ or $R_4$ is bonded to the amide carbon;

separating the product glycol aldehyde from the reaction mixture.

2. A process as claimed in claim 1 wherein carbon monoxide and hydrogen are present in mole ratios ranging from 20 to 1 to 1 to 20 $CO/H_2$.

3. A process as claimed in claim 1 wherein the superatmospheric pressures range from about 140 to 280 atmospheres.

4. A process as claimed in claim 1 wherein the elevated temperatures range from about 50° to 150° C.

5. A process as claimed in claim 1 wherein M is rhodium.

6. A process as claimed in claim 1 wherein X is an anion selected from the group of chlorides, hydrides, and trifluoroacetates.

7. A process as claimed in claim 1 wherein $R_1$ is aromatic.

8. A process as claimed in claim 1 wherein $R_2$ is aliphatic and comprised of only carbon and hydrogen atoms.

9. A process as claimed in claim 1 wherein an additional organophosphine group is incorporated into at least one of the $R_3$ or $R_4$ groups.

10. A process as claimed in claim 1 wherein at least one of $R_3$ and $R_4$ can range from about 10 to about 100 carbon atoms.

11. A process as claimed in claim 10 wherein the catalyst complex exhibits a substantial solubility in non-polar organic solvents, thereby substantially improving the glycol aldehyde product and catalyst separation and recycling operations.

12. A process as claimed in claim 1 wherein the catalyst compound is rhodium N-methyl, N-octadecyl-3-diphenylphosphinopropionamide.

13. A process as claimed in claim 10 wherein the non-polar organic solvent is selected from the group of toluene, xylene, and mixtures thereof.

* * * * *